(12) United States Patent
Zheng et al.

(10) Patent No.: US 9,898,583 B2
(45) Date of Patent: Feb. 20, 2018

(54) ZOOM PANE FOR A CENTRAL MONITORING DEVICE

(75) Inventors: Chuan Zheng, Bedford, MA (US); Kathleen R. Meschisen, Acton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1303 days.

(21) Appl. No.: 12/866,068

(22) PCT Filed: Feb. 2, 2009

(86) PCT No.: PCT/IB2009/050413
§ 371 (c)(1),
(2), (4) Date: Aug. 4, 2010

(87) PCT Pub. No.: WO2009/107006
PCT Pub. Date: Sep. 3, 2009

(65) Prior Publication Data
US 2011/0010193 A1    Jan. 13, 2011

Related U.S. Application Data

(60) Provisional application No. 61/031,372, filed on Feb. 26, 2008.

(51) Int. Cl.
*G06Q 50/22*    (2012.01)
*G06F 19/00*    (2018.01)

(52) U.S. Cl.
CPC ......... *G06F 19/3406* (2013.01); *G06Q 50/22* (2013.01); *G06F 19/3418* (2013.01); *G06F 19/3487* (2013.01)

(58) Field of Classification Search
None
See application file for complete search history.

(56) References Cited

U.S. PATENT DOCUMENTS 5,262,944 A * 11/1993 Weisner ................. A61B 5/044
  128/922
5,331,549 A * 7/1994 Crawford, Jr. ...... G06F 19/3406
  600/513

(Continued)

FOREIGN PATENT DOCUMENTS

CN    1517062 A    8/2004
EP    0569670 A2    11/1993

(Continued)

OTHER PUBLICATIONS

Levine et al., "Windows XP: The Complete Reference" Oct. 2001.*
Honeywell, "FVMS Network Video Management Software" Apr. 27, 2005.*

Primary Examiner — Neal Sereboff

(57) ABSTRACT

In a clinical environment, where multiple patients reside at any given time, central patient monitoring stations (10), such as nurses stations exist to consolidate information gathered concerning physiological parameters of the patients. The data is displayed in several panes (22) of a display (18) of the monitoring station (10). Due to certain size limitations of the display (18), it is often difficult to discern the data displayed on the panes (22), or to even display all of the data that is being gathered. A user can enlarge any given pane (22) into a zoomed pane (32) that offers greater functionality of any other pane (22), without completely obscuring, or adjusting the size of any other pane (22).

14 Claims, 6 Drawing Sheets

(56) References Cited

U.S. PATENT DOCUMENTS

| | | | | |
|---|---|---|---|---|
| 5,712,995 | A * | 1/1998 | Cohn | G06F 3/0481 |
| | | | | 715/792 |
| 5,943,053 | A * | 8/1999 | Ludolph | G06F 3/0481 |
| | | | | 715/790 |
| 6,025,841 | A * | 2/2000 | Finkelstein | G06F 3/0481 |
| | | | | 715/803 |
| 6,704,034 | B1 | 4/2004 | Rodriguez et al. | |
| 6,731,311 | B2 * | 5/2004 | Bufe | G06F 19/3418 |
| | | | | 600/301 |
| 6,907,576 | B2 * | 6/2005 | Barbanson | G06F 3/0481 |
| | | | | 707/E17.121 |
| 7,363,073 | B2 * | 4/2008 | Nonaka | A61B 5/024 |
| | | | | 600/483 |
| 7,487,454 | B2 * | 2/2009 | Czerwinski | G06F 3/0481 |
| | | | | 715/751 |
| 7,797,640 | B2 * | 9/2010 | Baumann | H04N 7/181 |
| | | | | 715/781 |
| 8,058,986 | B2 | 11/2011 | Klabunde et al. | |
| 2002/0171682 | A1 * | 11/2002 | Frank | H04N 1/00411 |
| | | | | 715/772 |
| 2002/0196141 | A1 * | 12/2002 | Boone | G08B 29/186 |
| | | | | 340/523 |
| 2003/0076363 | A1 | 4/2003 | Murphy | |
| 2003/0208465 | A1 * | 11/2003 | Yurko | G06F 19/322 |
| 2003/0229900 | A1 * | 12/2003 | Reisman | G06F 17/30873 |
| | | | | 725/87 |
| 2005/0229110 | A1 * | 10/2005 | Gegner | G06F 3/0481 |
| | | | | 715/800 |
| 2005/0240873 | A1 * | 10/2005 | Czerwinski | G06F 3/0481 |
| | | | | 715/740 |
| 2006/0229557 | A1 * | 10/2006 | Fathallah | G06F 19/3468 |
| | | | | 604/131 |
| 2007/0016875 | A1 * | 1/2007 | Santos-Gomez | G06F 3/0481 |
| | | | | 715/798 |
| 2007/0055947 | A1 | 3/2007 | Ostojic et al. | |
| 2007/0074129 | A1 * | 3/2007 | Baumann | H04N 7/181 |
| | | | | 715/764 |
| 2007/0106753 | A1 * | 5/2007 | Moore | G06F 17/3089 |
| | | | | 709/217 |
| 2007/0171238 | A1 | 7/2007 | Ubillos et al. | |
| 2007/0198942 | A1 | 8/2007 | Morris | |
| 2008/0034381 | A1 * | 2/2008 | Jalon | G06F 17/30126 |
| | | | | 719/329 |
| 2008/0307343 | A1 * | 12/2008 | Robert | G06F 3/04817 |
| | | | | 715/765 |
| 2009/0054735 | A1 * | 2/2009 | Higgins | A61B 5/0006 |
| | | | | 600/300 |
| 2010/0318511 | A1 * | 12/2010 | Phan | G06F 17/30958 |
| | | | | 707/722 |

FOREIGN PATENT DOCUMENTS

| | | |
|---|---|---|
| JP | 716352 A | 6/1995 |
| JP | 2007017247 A | 1/2007 |

* cited by examiner

ZOOM PANE FOR A CENTRAL MONITORING DEVICE

CROSS REFERENCE TO RELATED APPLICATIONS

This application claims the benefit of U.S. provisional application Ser. No. 61/031,372 filed Feb. 26, 2008, which is incorporated herein by reference.

The present application relates to medical monitoring devices. It bears particular application in improving accessibility of patient information on a central monitoring device and will be described with particular reference thereto. It is to be appreciated, however, that the present application can be used for any display that displays multiple data sets or parameters concurrently, and is not necessarily limited to the aforementioned application.

On a central monitoring device, a display is divided into multiple viewing areas or panes, each pane representing several parameters of a single patient that are currently being monitored. Presently, central monitoring devices allow for expanded viewing the pane of a single patient while concurrently viewing the panes of other patients. Typically, this view is placed at the bottom of the screen while the other viewing panes are squeezed into the remaining space at the top of the viewing screen, as shown in FIG. 1. The shrunken panels become barely legible. In the illustrated example, the display for bed 5 becomes prominent at the bottom of the display, but all of the other displays are squeezed into about half of their original area.

The present application provides a new and improved central monitoring device display which overcomes the above-referenced problems and others.

In accordance with one aspect, a patient monitoring station is provided. The monitoring station receives and displays patient data. A display displays a plurality of panes. A controller controls the display such that each pane displays selected patient data such that each pane is selectable by a user to become an enlarged, zoomed pane without affecting a size of any other of the plurality of panes.

In accordance with another aspect, a method of displaying monitored parameters is provided. At least one monitored parameter associated with a patient is displayed in one of a plurality of panes of a display. One of the plurality of panes is selected to become an enlarged, zoomed pane. The zoomed pane is enlarged without affecting a size of any other of the plurality of panes.

In accordance with another aspect, a patient monitoring device that compiles data concerning a plurality of patients on a display including a plurality of panes, each pane being associated with a single patient is provided. The monitoring device includes an enlarged, zoomed pane that is anchored to the position of a selected underlying pane that partially, but not completely, obscures neighboring panes without adjusting a size of any other of the plurality of panes.

One advantage is that a user can zoom in on a selected pane without shrinking other panes.

Another advantage lies in the utility of an icon toolbar that appears in the enlarged pane.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
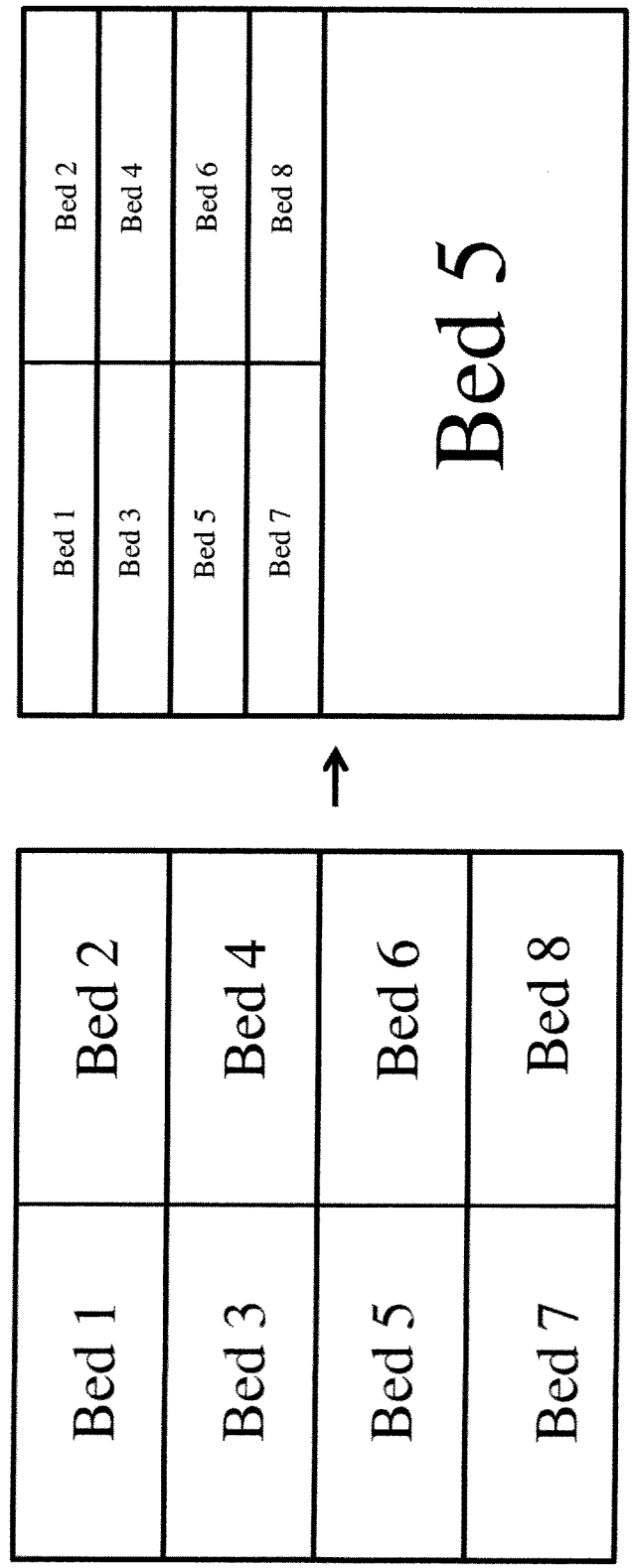
FIG. 1 is prior art rendition of an existing central display monitor.
Figure 2:
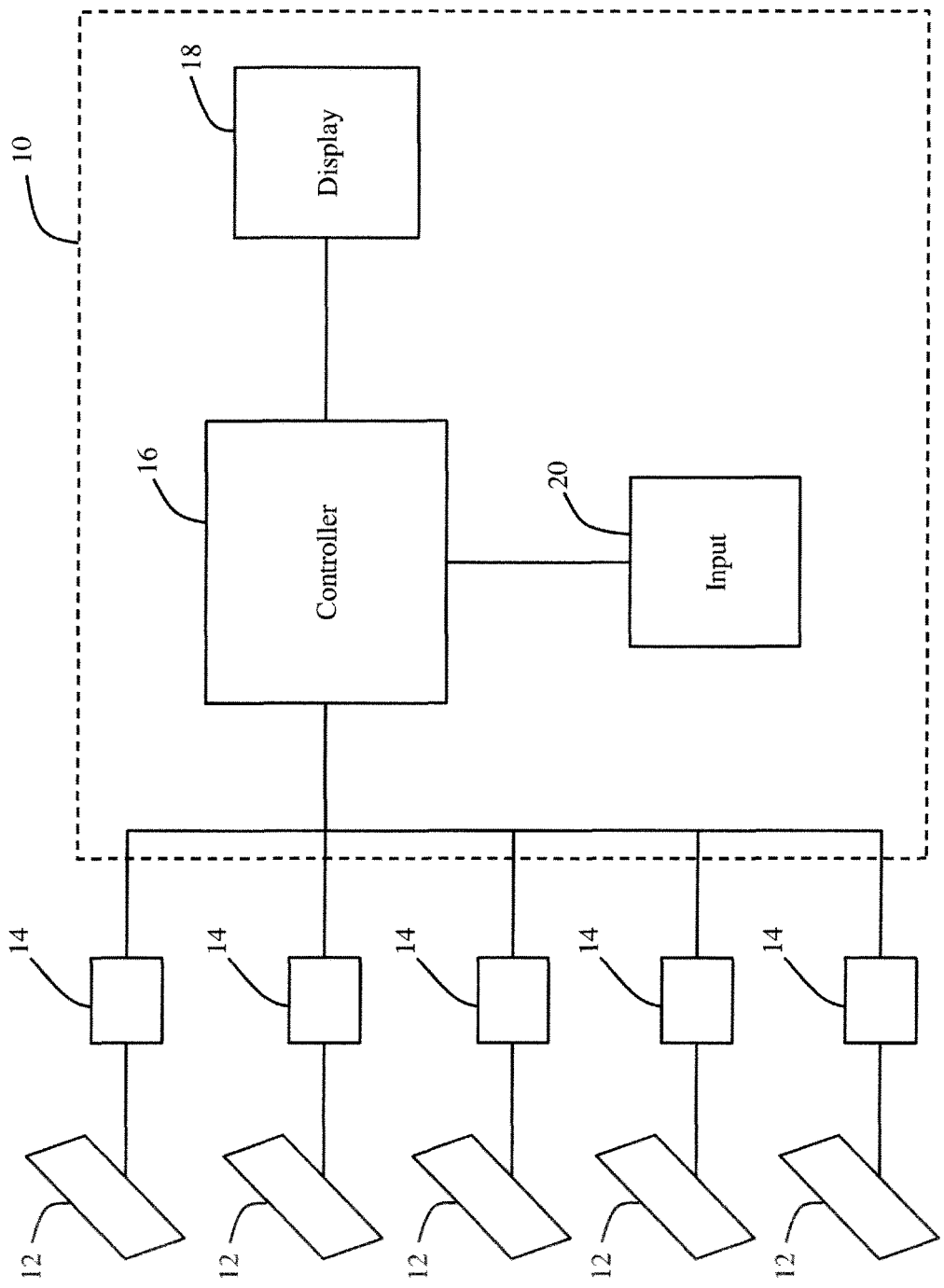
FIG. 2 is a diagrammatic illustration of a central display monitor in accordance with the present application.

With reference to FIG. 2, a central monitoring station 10 monitors several patient beds 12. The central monitoring station 10, as its name implies, is preferably centrally located in reference to the beds 12 that it monitors, such as a nurse's station, or the like. Each patient in one of the patient beds 12 has multiple sensors that monitor various parameters of the patient's physiology. These sensors can include ECG sensors, IV fluid pumps, blood pressure sensors, $SpO_2$ sensors, pulse sensors, thermometers, respiratory sensors, and exhaled gas sensors. Of course, other sensors can be associated with a patient, and not all of the above-mentioned sensors have to be associated with a patient at any given time.

The sensors report to a local buffer 14. The buffer 14 serves as a gathering point for all the data collected by the sensors, and provides temporary storage for the data. The local buffer 14, for example may be a patient's bedside monitor that travels with the patient. The local buffer 14 may also be a more permanent fixture, such as a wall-mounted monitor that is permanently associated with a certain bed, alcove, or room. The communication links between the sensors and the local buffer 14 may be wireless, hard wired, or a combination of both. Similarly, the sensors may be powered by battery, external AC power, or a combination of both.

The local buffers 14 then communicate with the central monitoring device 10. A controller 16 receives input from the buffers 14 of as many patient beds 12 for which the central monitoring station 10 is responsible. The controller 16 then directs a display 18 of the central monitoring station 10 to display the information received from the buffers 14. The central monitoring station 10 also includes a user interface 20 that allows the user to view and/or manipulate the data displayed on the display 18. The interface 20 can be a separate component or integrated into the display 18 such as with a touch screen monitor. The communications links between the buffers 14 and the central monitoring station 10 may be wireless. If the buffer 14 were embodied, for example, in a local monitor mounted on an IV stand, the patient could leave the immediate vicinity, but take the buffer 14 along. Wireless communication between the buffer 14 and the central monitoring station 10 allows greater mobility for the patient while still being able to monitor the selected parameters of the patient. If the buffer 14 is embodied in a more permanent fixture, the communications links between the buffers 14 and the central monitoring station 10 may be hard lines, such as standard Ethernet network cables.

Figure 3:
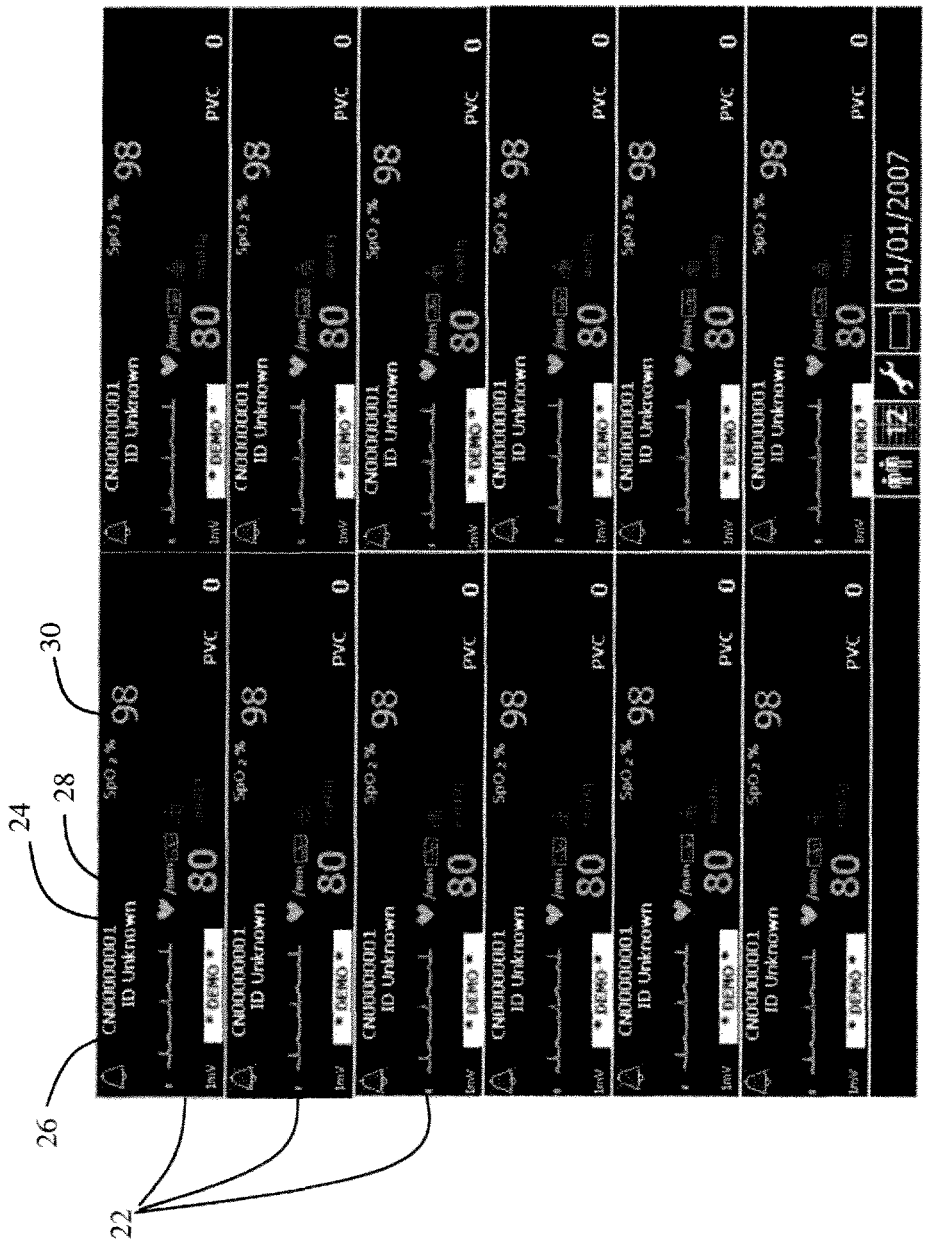
FIG. 3 is a twelve pane display with no panes zoomed.

As mentioned previously, the controller 16 directs the display 18 to display the information received from the various buffers 14. With reference now to FIG. 3, the display 18 of the central monitoring station 10 is divided into panes, 22 each pane 22 representing information received from one buffer device 14, that is, from one patient. Twelve panes 22 are illustrated in FIG. 3, but more or fewer panes are also contemplated. The number of panes per central monitoring station could be dictated by the size of the display 18 and the patient-to-central monitoring station 10 ratio, and other factors.

As illustrated, the upper left pane 22 (as well as the rest of the panes 22) of the display 18 has various sub-displays corresponding to the information received from the buffer 14. For example, the pane 22 has a patient ID sub-display 24 where the patient's name, bed or room number, and other identifying information, such as a unique hospital ID are displayed. An ECG sub-display 26 displays the latest ECG readings received from the buffer 14 about the patient. A pulse sub-display 28 displays the latest pulse readings of the patient. An $SpO_2$ sub-display 30 displays the latest blood oxygenation reading from the patient. There may also be invasive blood pressure (IBP), end tidal $CO_2$ (et$CO_2$) and respiration displays. Typically, due to space limitations, only three or four values can be displayed on the pane 22. Each additional pane displays similar information, with the exception that a separate pane represents a separate patient. Also, each pane can be configured independently.

Figure 4:
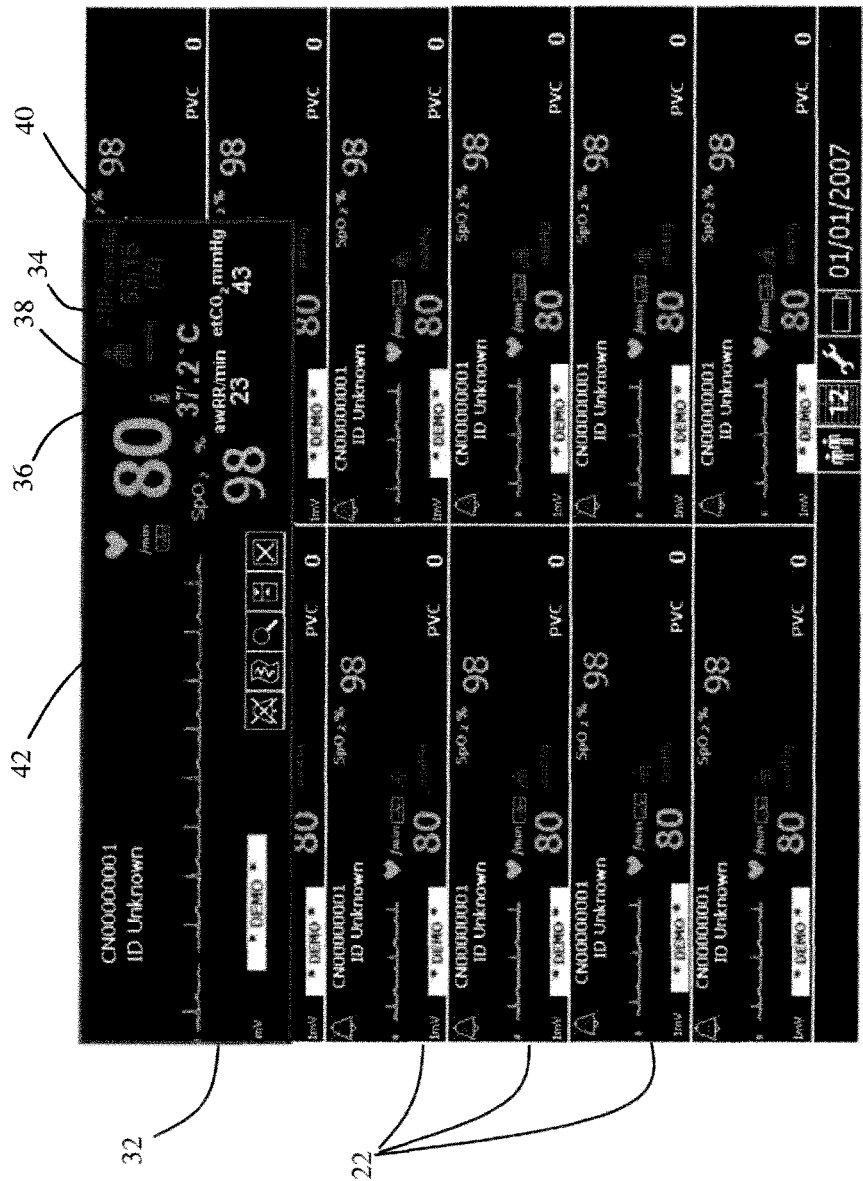
FIG. 4 is a twelve pane display with one corner pane zoomed.
Figure 5:
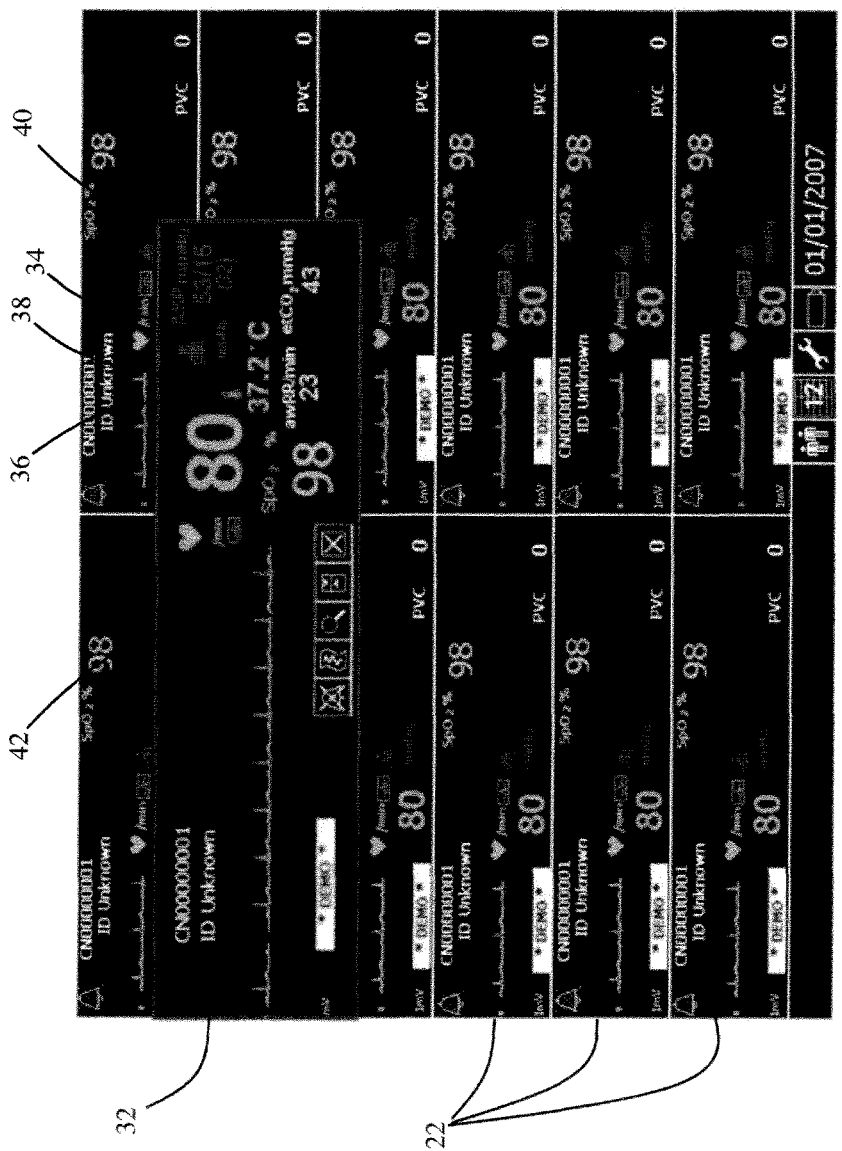
FIG. 5 is a twelve pane display with the second pane of the left column zoomed.

With reference now to FIG. 4, by using the interface 20 the user can select one of the panes 22 and enlarge it to view a zoomed pane 32. In the touch screen embodiment, the user can touch the pane to enlarge it. In FIG. 4, the user has selected the top left pane and enlarged it. The zoomed pane 32 is enlarged so that it is substantially larger than the other panes 22, yet positioned so that it does not fully obscure any other pane 22. The enlarged pane 32 obscures some, but not all of each adjacent pane. In FIG. 5, the user has selected the pane 22 that is second from the top and on the left to enlarge. As with the corner enlarged pane 32 of FIG. 4, the enlarged pane 32 of FIG. 5 obscures some, but not all of each adjacent pane 22.

Figure 6:
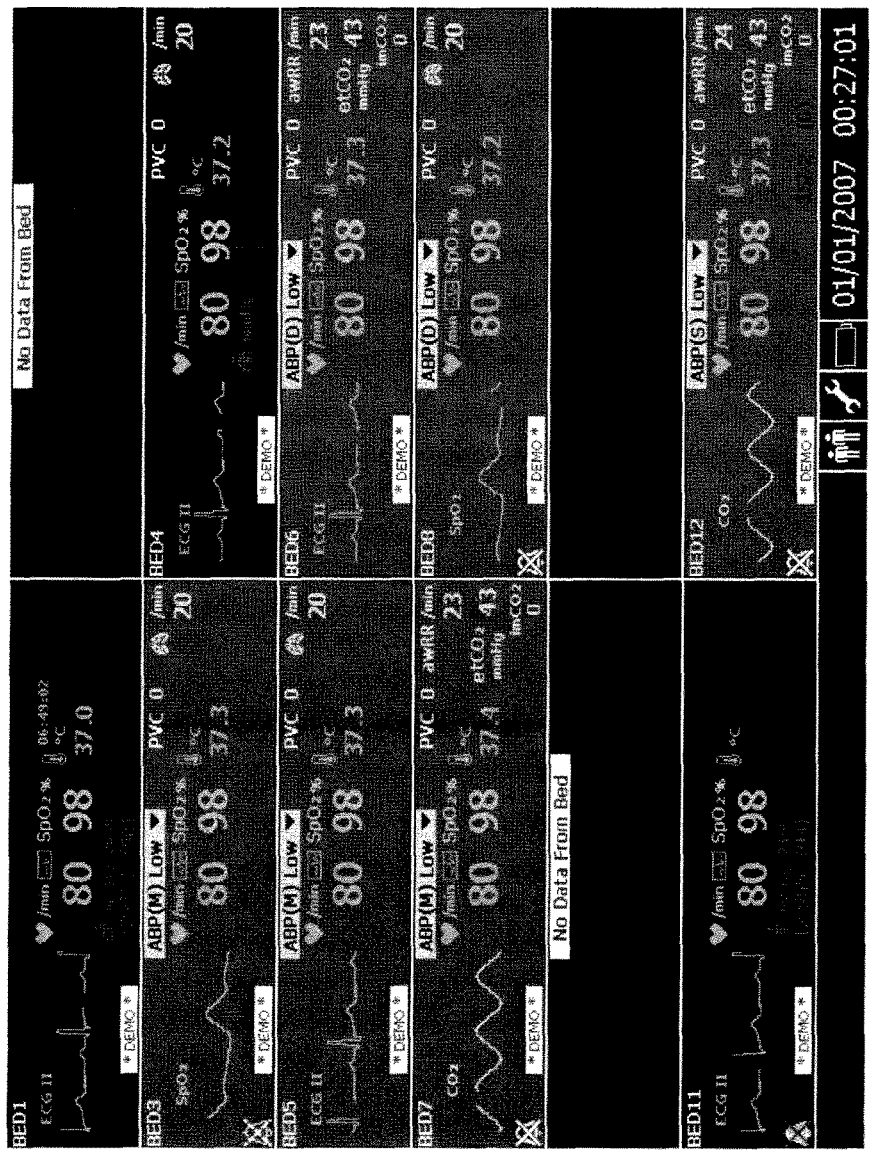
FIG. 6 is a display with multiple alarms activated.

If one or more of the patients' monitored parameters drops to a critical level, the controller 16 typically triggers an alarm, such as flashing the pane 22 a different color, or issuing an audible alarm, or the like, or a combination thereof. With reference to FIG. 6, beds 3, 5, 6, 7, 8 and 12 are issuing alarms, while beds 1, 4, and 11 are displaying normal values. The zoomed panes 32 shown in FIGS. 4 and 5 allow the user to still see an alarm on a pane 22 that is not currently enlarged because it will not be completely obscured by the zoomed pane 32. Preferably, the zoomed pane 32 is enlarged in-place and anchored, otherwise it would be possible to move it to a position that would completely obscure another pane 22. Optionally, the pane could be movable but constrained such that it cannot be positioned fully covering another pane.

With Reference again to FIGS. 4 and 5, the extra space of the zoomed pane 32 allows not only larger displays of the parameters that were displayed in the typical sized pane 22, but it also allows space for the display of additional parameters. For example, a larger ECG display 26 can be accommodated. In one embodiment, the zoomed pane 32 allows at least 30 mm of vertical space in which to display an ECG waveform. An arterial blood pressure display 34 displays the blood pressure of the patient. A temperature display 36 displays the current or latest temperature of the patient. An airway respiration sub-display 38 displays the latest or average times per minute the patient breathes. An end tidal $CO_2$ concentration sub-display 40 displays the concentration of $CO_2$ that the patient is exhaling. Again, the size of the selected displays and which displays are actually displayed in the zoomed waveform are customizable by the user.

It is to be understood that additional or other parameters could be displayed, the aforementioned parameters are provided by way of example. In one embodiment, all of the parameters that are capable of being monitored at any given time are monitored, this includes times when a parameter is not being displayed because its pane 22 is not zoomed or it is obscured by a zoomed pane 32. Just because it is not displayed does not mean that the parameter is not being monitored. Thus, even a hidden parameter can trigger an alarm if the processor 16 determines that it has entered a critical state.

Additionally, when a pane 22 is selected and zoomed, the user gains access to an icon toolbar 42 that displays selectable icons that offer the user additional control and customizability with respect to the currently zoomed pane 32. For example, the icon toolbar may include an audible alarm icon. The user can toggle this icon to turn an audible alarm on or off. In one embodiment, the on screen alarm is always enabled. Another icon opens a dialog box that allows the user to print the current zoomed display 32. Another icon allows the user to further zoom any portion of the zoomed display. In one embodiment, the further zoomed portion does not extend beyond the boundaries of the zoomed pane 32, such that other panes 22 do not become completely obscured. Another icon allows the user to customize the parameter monitoring of the given patient. For example, if the system currently takes the patient's blood pressure every thirty minutes, but the user desires more frequent updates, they can set the blood pressure to be taken every twenty minutes, or however frequently is appropriate. Also, there is an icon that the user can select to minimize the zoomed pane 32 back to its original size. In one embodiment, the zoomed pane 32 will automatically minimize after a period of inactivity. In one particular embodiment, the zoomed pane 32 automatically minimizes after two minutes of inactivity.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A patient monitoring network comprising:
   a plurality of physiological parameter monitoring devices for monitoring physiological parameters of each of a plurality of patients;
   at least one data buffer configured to temporarily store the monitored physiological parameters of each of the patients from the at least one parameter monitoring device; and
   a patient monitoring station for displaying at least a portion of the monitored physiological parameters, the patient monitoring station including:
   a display device,
   a display device controller programmed to control the display device to:
   display a plurality of panes, each pane corresponding to a corresponding patient,
   display in each pane a portion of the monitored physiological parameters from the at least one data buffer of the corresponding patient,
   enlarge and anchor a user selected from one of the displayed panes in-place to create a zoomed pane without reducing a size of non-selected panes and only partially overlapping adjacent non-selected panes, display a greater amount of the monitored physiological parameters in the zoomed pane than in the selected pane before enlarging.

2. The patient monitoring network as set forth in claim 1, wherein the display device controller is further programmed to control the display device to:
change an appearance of one or more of the panes to change appearance indicative of an alarm condition in response to one or more of the monitored physiological parameters of the patient corresponding to the monitored physiological parameter reaching a preselected alarm level, the zoomed pane only partially overlapping the adjacent non-selected panes such that part of the adjacent pane is not obscured by the zoomed pane such that the change in appearance of the adjacent pane indicative of the preselected alarm level is visible to a viewer of the display device.

3. The patient monitoring network as set forth in claim 1, wherein the display device controller controls the display to display the panes in columns with the panes that are not zoomed all the same size.

4. A method of displaying monitored physiological parameters of each of a plurality of monitored patients comprising:
on a display device, displaying a plurality of panes, each pane corresponding to one of the patients and displaying an identifier of the corresponding patient;
with a controller, receiving physiological parameters monitored by patient physiological parameter sensors and controlling the display device to display at least one of the monitored physiological parameters of the corresponding patient and an identifier of the corresponding patient in the corresponding pane;
indicating a selected one of the plurality of panes to become an enlarged, zoomed pane using a user input device;
controlling the display device to enlarge the selected pane into the zoomed pane without affecting a size of any other of the plurality of panes using the controller, the zoomed pane partially overlaying and obscuring portions of panes adjacent the zoomed pane without completely overlaying any other pane;
changing an appearance of one or more of the displayed panes using the controller such that the change in appearance of the non-overlaid portion of one of the overlaid pane is visible to the user.

5. The method as set forth in claim 4, further including: anchoring the zoomed pane in-place on the display deviceusing the controller.

6. The method as set forth in claim 4, further including: controlling the display device to display additional information on the zoomed pane that is not displayed before the selected pane is zoomed using the controller.

7. The method as set forth in claim 4, wherein the step of displaying additional information includes displaying a greater amount of waveform information.

8. The method as set forth in claim 4, wherein the step of displaying additional information includes displaying a greater number of the monitored physiological parameters.

9. The method as set forth in claim 4, further including: using the controller to control the display device to display an icon toolbar on the zoomed pane that includes user selectable icons for interacting with the current zoomed pane.

10. The method as set forth in claim 9, further including: changing which physiological parameters of the patient corresponding to the zoom pane are displayed in the zoomed pane.

11. The method as set forth in claim 4, wherein the controller changes the appearance of the one or more displayed panes in response to the monitored physiological parameters of the patient corresponding to the pane triggering an alarm condition.

12. The method as set forth in claim 4, wherein the panes are opaque.

13. A non-transitory computer readable medium carrying software which when loaded on a processor controls an attached display of a multi-patient monitor to perform the steps of:
displaying monitored physiological parameters and a patient identifier corresponding to each of a plurality of patients in a corresponding one of a plurality of panes arranged in one or more columns on the display;
enlarging a user selected one of the plurality of panes, enlarging the selected pane from a non-zoomed state to a zoomed state without affecting a size of any other of the plurality of panes such that the zoomed state pane obscures a first part of an adjacent pane and does not obscure a second part of the adjacent pane; and
changing an appearance of the partially obscured adjacent pane to indicate an alarm condition of the patient corresponding to the partially obscured adjacent pane , such that the change in appearance of the second part of the partially obscured adjacent pane indicative of the alarm condition is visible to the user of the display device.

14. The non-transitory computer-readable medium as set forth in claim 13, wherein the panes are displayed in two columns and are opaque.

* * * * *